United States Patent
Schoenbach et al.

(10) Patent No.: US 9,724,011 B2
(45) Date of Patent: Aug. 8, 2017

(54) WIDEBAND BIO-IMAGING SYSTEM AND RELATED METHODS

(71) Applicant: OLD DOMINION UNIVERSITY RESEARCH FOUNDATION, Norfolk, VA (US)

(72) Inventors: Karl H. Schoenbach, Norfolk, VA (US); Shu Xiao, Norfolk, VA (US)

(73) Assignee: OLD DOMINION UNIVERSITY RESEARCH FOUNDATION, Norfolk, VA (US)

( * ) Notice: Subject to any disclaimer, the term of this patent is extended or adjusted under 35 U.S.C. 154(b) by 0 days.

(21) Appl. No.: 14/885,023

(22) Filed: Oct. 16, 2015

(65) Prior Publication Data
US 2016/0106335 A1    Apr. 21, 2016

Related U.S. Application Data

(62) Division of application No. 12/809,007, filed as application No. PCT/US2008/087754 on Dec. 19, 2008, now Pat. No. 9,173,584.

(60) Provisional application No. 61/016,363, filed on Dec. 21, 2007.

(51) Int. Cl.
*A61B 5/05* (2006.01)
*A61B 6/03* (2006.01)

(52) U.S. Cl.
CPC .............. *A61B 5/0507* (2013.01); *A61B 5/05* (2013.01); *A61B 6/03* (2013.01); *A61B 2576/00* (2013.01)

(58) Field of Classification Search
CPC ...... A61B 5/0507; A61B 2576/00; A61B 6/03

USPC ........................................................ 324/663
See application file for complete search history.

(56) References Cited

U.S. PATENT DOCUMENTS

| | | | |
|---|---|---|---|
| 3,801,773 A | 4/1974 | Matsumi | |
| 6,845,253 B1 | 1/2005 | Schantz | |
| 7,809,427 B2 | 10/2010 | Winters et al. | |
| 2005/0107693 A1 | 5/2005 | Fear et al. | |
| 2006/0239404 A1 | 10/2006 | Udpa et al. | |
| 2010/0278401 A1* | 11/2010 | Schoenbach | A61B 5/05 382/128 |

OTHER PUBLICATIONS

Baum et al., "Focal waveform of a prolate-spheroidal impulse-radiating antenna (IRA)", Radio Science (2007) 42(6). (11 pages).
Bolomey et al., "Microwave diffraction tomography for biomedical applications", IEEE Trans Microwave Theory Tech (1982) 30: 1990-2000.
Chew et al., "A frequency-hopping approach for microwave imaging of large inhomogeneous bodies", IEEE Microwave and Guided Wave Letters (1995) 5: 439-441.

(Continued)

*Primary Examiner* — Thomas Valone
(74) *Attorney, Agent, or Firm* — Nixon Peabody LLP; Eduardo J. Quinones (57) ABSTRACT

An imaging and recordation system is provided. The system includes a high-power, focusing antenna for illuminating biological tissue. The system further includes a power source for powering the antenna. The system further includes a data acquisition module, for recording the dielectric properties of tissues illuminated by the high-power, focusing antenna. The system illuminates the tissues using ultrashort electrical pulses.

5 Claims, 9 Drawing Sheets

(56) References Cited

OTHER PUBLICATIONS

Fear et al., "Experimental feasibility study of confocal microwave imaging for breast tumor detection", IEEE Trans Microwave Theory Tech (2003) 51: 887-892.
Haddadin et al., "Imaging strongly scattering media using a multiple frequency distorted Born iterative method", IEEE Trans on Ultrasonics, Ferroelectrics and Frequency Control (1998) 45: 1485-1496.
Hagness et al., "Two-dimensional FDTD analysis of a pulsed microwave confocal system for breast cancer detection: fixed-focus and antenna-array sensor", IEEE Trans Biomedical Engineering (1998) 45(12): 1470-1479.
Heeren et al., "250 kV sub-nanosecond pulse generator with adjustable pulse-width", IEEE Trans Diel Electr Insul (2007) 14: 884-888.
Moghaddam et al., "Nonlinear two-dimensional velocity profile inversion using time domain data", IEEE Transactions on GeoScience and Remote Sensing (1992) 30(1): 147-156.
Semenov et al., "Dielectric spectrometry of canine myocardium during ischemia and hypoxia at frequency spectrum from 100kHz to 6GHz", IEEE Trans Medical Imaging (2002) 21(6): 703-707.
International Search Report and Written Opinion mailed Feb. 12, 2009 for counterpart PCT Application No. PCT/US2008/087754.

\* cited by examiner

WIDEBAND BIO-IMAGING SYSTEM AND RELATED METHODS

CROSS REFERENCE TO RELATED APPLICATIONS

This application is a divisional of U.S. National Stage application Ser. No. 12/809,007, filed Jun. 17, 2010, which is a §371 national phase entry of International Application No. PCT/US2008/87754, filed Dec. 19, 2008, which claims priority to U.S. Provisional Patent Application No. 61/016,363, filed Dec. 21, 2007, all of which are hereby incorporated by reference in their entireties.

FIELD OF THE INVENTION

The present invention is related to the field of imaging, and more particularly, to systems and methods for imaging using electromagnetic waves.

BACKGROUND OF THE INVENTION

Microwave imaging can be used to determine the dielectric permittivity distribution of objects using measurements of a scattered electric field. In a biological context, such imaging of biological tissues having different dielectric permittivities results in different scattering cross sections. The contrast obtained with this imaging is generally greater than that obtained with x-ray radiography, which is on the order of a few percent. Since the electrical conductivity and dielectric constant of tumors, for example, are an order of magnitude higher than normal tissue over a wide frequency range, typically the range of $10^7$-$10^{10}$ Hz, tumors can be readily differentiated from the normal tissue. Moreover, with such imaging irregular physiological changes resulting from the deterioration of health can also be monitored.

Conventional microwave imaging is predominantly based on narrowband technology and records scattered signals at a single frequency, or alternatively, at multiple frequencies recorded at different times. A pulsed microwave imaging system on the other hand, contains a wide range of frequencies. For example, a Gaussian-pulse varies in time according to the following relation:

$$g(t) \alpha \exp(-t^2/a^2); \text{ and} \quad (1)$$

the corresponding frequency range is given by $$G(f) \alpha \exp(-\pi^2 f^2/a^2). \quad (2)$$

For a=100 ps, which corresponds to a pulse with a width of 100 ps, the frequency range can extend to f0=5 GHz. Although microwave imaging in the time domain has been studied, typically only back-scattered signals have been utilized, in an approach to detect tumors in breast tissue.

SUMMARY OF THE INVENTION

The present invention is directed to systems and related methods for imaging and real-time recording of the dielectric properties of biological tissue. One of the varied aspects of the invention is utilization of ultrashort electrical pulses. The ultrashort electrical pulses, more particularly, can have durations on the order of 100 ps (i.e., more than 10 ps, but less than 100 ps).

BRIEF DESCRIPTION OF THE DRAWINGS

There are shown in the drawings, embodiments which are presently preferred. It is expressly noted, however, that the invention is not limited to the precise arrangements and instrumentalities shown.

DETAILED DESCRIPTION

The invention is directed to systems and methods for recording spatial and temporal changes in the electrical properties of tissues located in a human or an animal using ultrashort electrical pulses. The ultrashort electrical pulses, more particularly, can have durations on the order of 100 ps.

Figure 1:
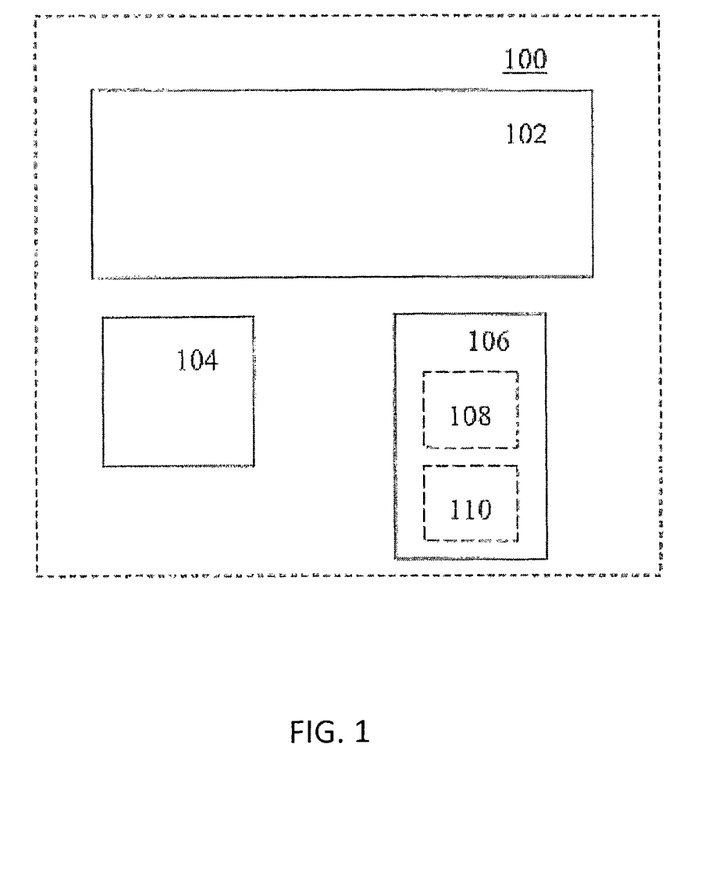
FIG. 1 is a schematic view of a system, according to one embodiment of the invention.

FIG. 1 is a schematic view of an imaging and real-time recordation system 100, according to one embodiment of the invention. The system 100 illustratively includes a high-power, focusing antenna 102 for illuminating tissues, a power source 104, and a data acquisition module 106. The focusing antenna, different embodiments of which are described more particularly below, is used to focus the radiation into the tissue. A focal point is then moved such that an entire volume of interest is scanned. The antenna 102 can produce a high electrical field pulse (>10 kV/cm at the focal point). This high power capability can achieve a high signal-noise ratio and facilitate detection of both backward scattering (reflection) and forward scattering (transmission), even if the signal is strongly attenuated in the tissue.

In one embodiment, the system 100 uses 100 ps pulses. Using 100 ps pulses, considering the diffraction-limit ($\lambda/2$), a resolution of a few millimeters can be obtained. The focusing ability of the system 100 allows 3-D scanning and filtering. The data acquisition module 106 can comprise fast-response electric field sensors 108. According to one embodiment, one or more of the electric field sensors 108 comprise ACD D dot sensors manufactured by Prodyn, which can record the free space electric field with a rise time of 50 ps.

The data acquisition 106 can further include one or more processors 110. The one or more processors 110 can be configured to execute, in dedicated circuitry and/or computer-readable code, image reconstruction algorithms in 3D FDTD inverse scattering, such as a gradient-based minimization algorithm.

According to one embodiment, the antenna 102 comprises an antenna system that includes a conical wave launching system and a reflector. The wave launching system 200 has rotational symmetry about the z-axis, as illustrated schematically in FIG. 2. The apex of the cone is at the first focal point F1. So, a wave emitted from F1 is a spherical TEM wave with its source at F1. The apex is connected to the inner conductor of a coaxial cable feed from one of the ends of the reflector. Such conical wave launcher above a ground plane is an unbalanced structure; thus, no balun is required to feed the wave launcher.

Figure 2:
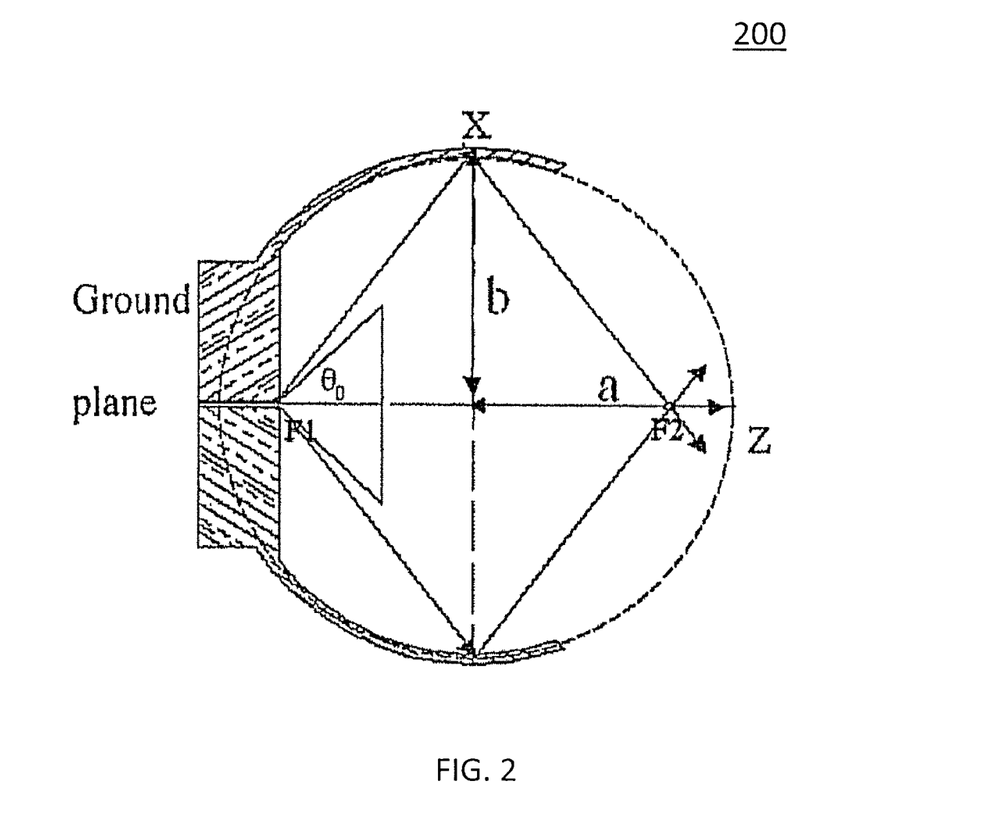
FIG. 2 is a schematic view of an antenna construct utilized in the system of FIG. 1, according to one embodiment of the invention.

The launched wave is reflected on the prolate spheroidal reflector surface to converge at the second focal point (F2). The electric field at F2 consists of prepulse, impulse and postpulse. The prepulse, caused by the diffraction at the edge of the wave launcher cone has the same polarity as the impulse, the scattered signal from the reflector. Due to rotational symmetry, the electric field at the second focal point has only longitudinal components.

In an alternative embodiment, the antenna 102 comprises a configuration that includes symmetrical conical arm feedings (either 4 or 2 arms) that from the first focal point to the reflector. A balun is used to suppress the common mode signal. The focused electrical field has its largest component in transverse direction.

Based on modeling results, using FDTD software Magic, the focusing pattern has an oval shape. Its size is 2-3 cm along the z axis and less than 1 cm along x axis for Full Width at Half Maximum (FWHM). The size of the focusing spot can be much smaller for smaller changes in signal amplitude. For example, recording changes at 90% of its peak increases the resolution to mm.

The focusing spot size typically does not fully determine the resolution of the imaging. The resolution is also determined by the quality of the collected scattered signal (e.g., the signal to noise ratio (SNR) and the quantity of the data, etc.) and the image reconstruction algorithm used in the inverse scattering process. Using nonlinear algorithms, it can be shown that the spatial resolution of the image can be improved to values of $1/7$ or $1/10$ of the wavelength, which is also referred to as the super-resolution.

The power source 104 comprises a high power pulse source that feeds the antenna 102 with durations on the order of 50 ps - 150 ps. This can be produced by a Marx generator charging a peaking capacitor with a peaking spark gap switch. Capacitors in the generator are displaced in a coaxial waveguide to minimize the stray inductance. High pressure gas is needed to minimize the peaking spark gap switch distance at a high hold-off voltage. Output voltages up to 500 kV, 100 ps can be generated from such generator. The resulting focused field at the second focal point is on the order of 10- 250 kV/cm. Other fast transient pulse source can be based on an inductive energy storage discharged through a solid-state opening switch (SOS). In both approaches, high frequency operation of >1 kHz is possible.

Signal attenuation in the human body can result in a low signal/noise ratio. For example, in normal breast tissue, the attenuation is close to 4 dB/cm for frequencies up to 10 GHz. The attenuation is due to Ohmic loss, but for impulses that cover a large frequency range, dispersion losses must be included. The variation of the index of refraction (or permittivity) with frequency, causes broadening of the pulse.

The complex permittivity of tissue can be described by a Debye model, in which only one relaxation time constant is taking into account, or Cole-Cole model, in which multiple relaxation time constants are included.

The propagation factor γ(f) is $$\gamma(f) = j2\pi f \sqrt{\epsilon_r}/c \qquad (3)$$

where $\epsilon_r$ is the dielectric permittivity of the medium and c is the speed of light in the vacuum. The distorted temporal pulse can be retrieved using an inverse Fourier transform:

$$v(t,z) = IFFT\{FFT[v(t,0)]\exp(-\gamma(f) \cdot z)\} \qquad (4)$$

Figure 3:
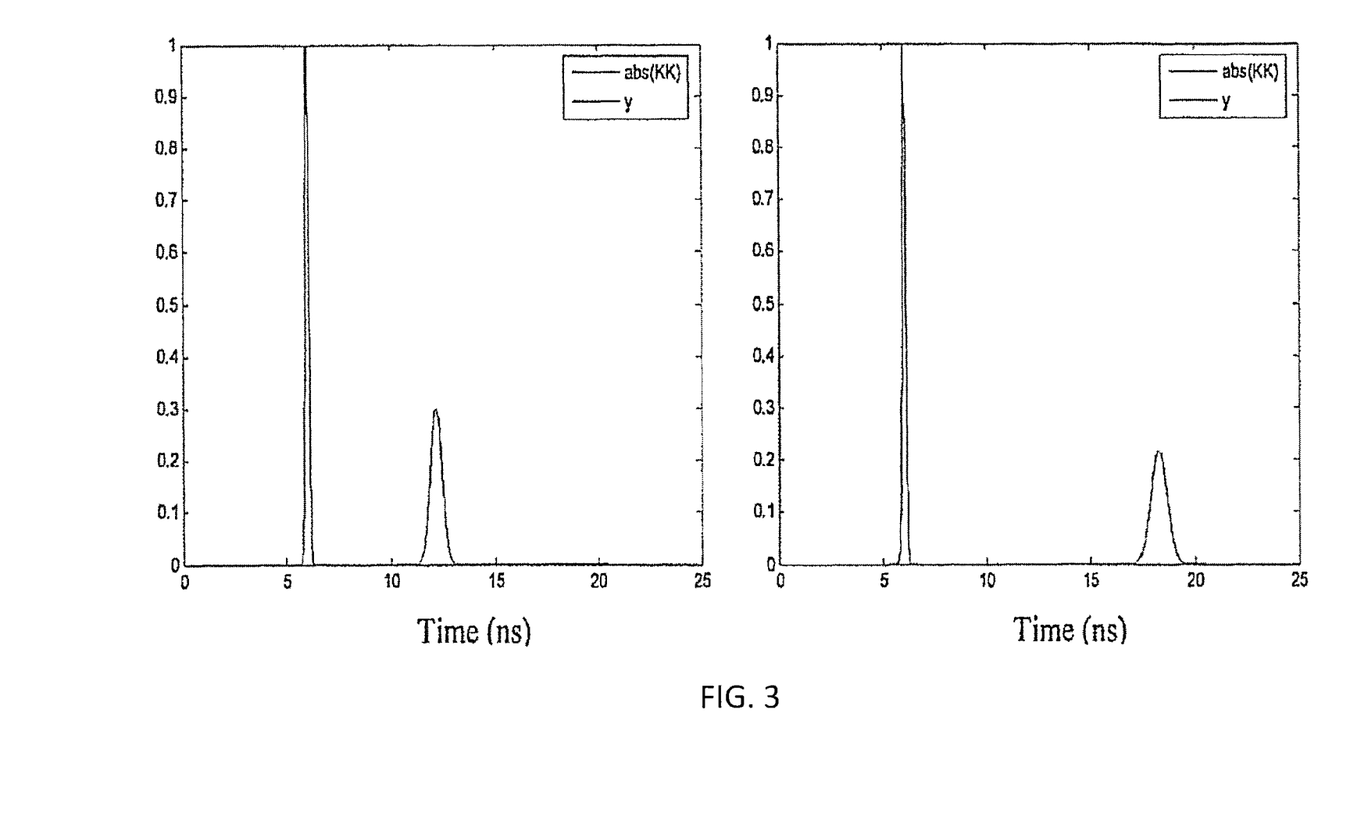
FIG. 3 is data representing Gaussian input impulse with respect to time.

For example, in water, which is a major constituent in the body, the dispersion can be calculated for a Gaussian input impulse with rise time (10-90%) of 140 ps. After the pulse travels 0.2 m and 0.4 m, the peak magnitude decreases to 30% and 20% respectively. Moreover, the pulse width broadens and the risetime increases to 370 ps and 480. FIG. 3 depicts this data.

A signal with a high amplitude is likely to alleviate problems of attenuation and dispersion. For example, a 100 kV/cm pulse allows a reduction of its signal by 50 dB, and still generates a signal in the range of a few V/cm. Using a high power radiation system, which radiates an impulse in a very short exposure time (on the order of 100 ps), allows the probing of deeper lying tissue despite high attenuation.

According to another embodiment of the invention, an imaging sequence is provided, which is implemented according to the following steps: 1) focusing the radiation into a site, where a tumor or other abnormality in permittivity could be located (at the focal point, tissue scatters the radiation into 4π (a full sphere), generally through Mie scattering); 2) recording both back scattered signal and forward scattered signal; and 3) processing data generated as a result and reconstructing 3-D images.

Figure 4A:
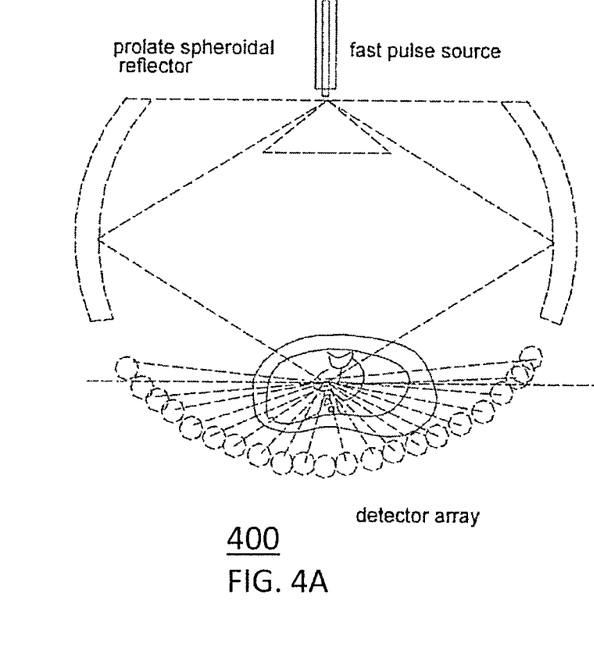
FIGS. 4A and 4B are a schematic illustration of 3-D scanning of tissue by changing the focal point of the antenna by adjusting the position of the antenna (FIG. 4A) or by adjusting the position of the patient (FIG. 4B).
Figure 4B:
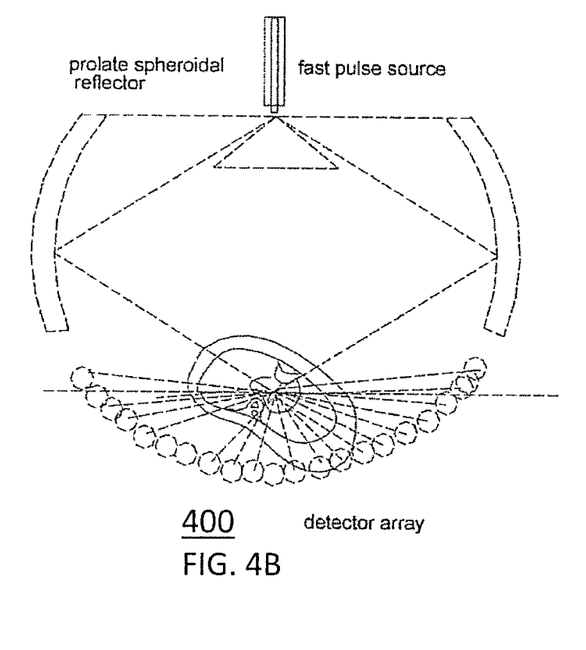

The focusing capability of the radiation system allows scanning of the tissue in three dimensions. As the focal point of the radiation antenna changes, the scattered signal from the tissue contains the information of the distribution of the complex dielectric permittivity in 3-D. Scanning can be done either by adjusting the position of patient or the position of the antenna as shown by system 400 in FIGS. 4A and 4B.

Figure 5:
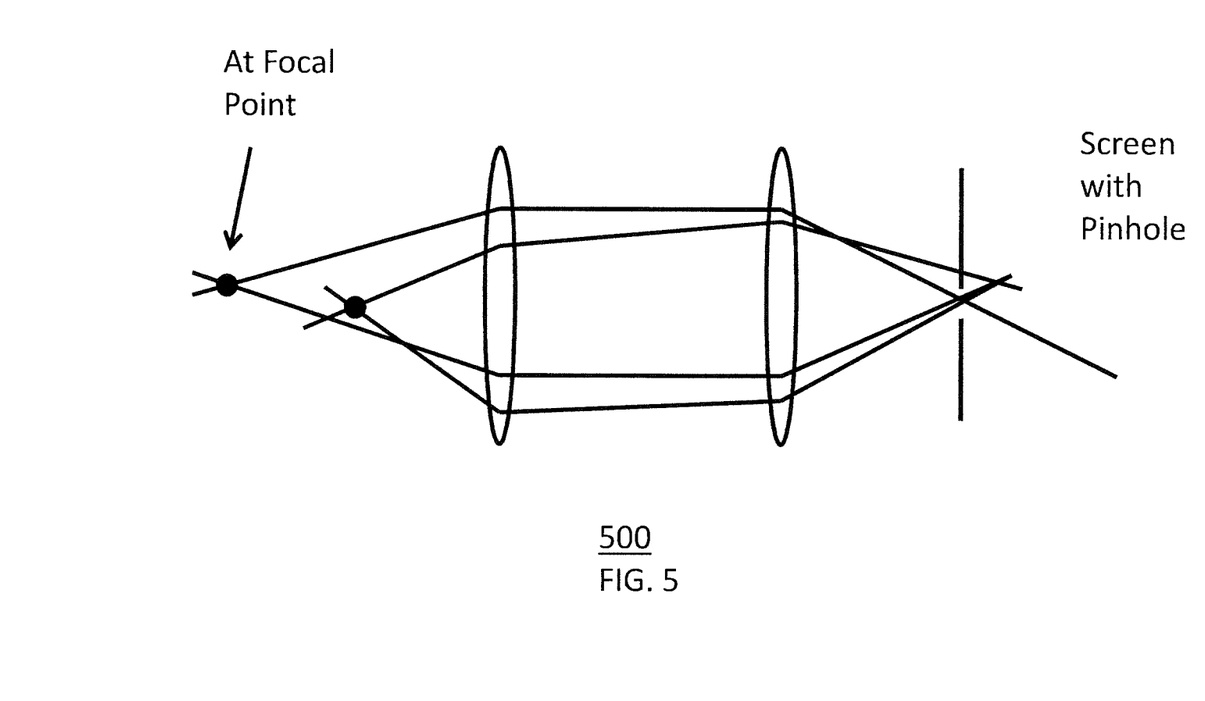
FIG. 5 is a schematic illustration of a confocal imaging system.

The focusing capability of the antenna allows the realization of the confocal microwave imaging. A confocal imaging system can be used generally to record fluorescence. A laser beam with one wavelength will be focused at the focal point illuminating the object to excite the dye molecules, which fluoresce at a longer wavelength. Confocal technology typically only allows the fluorescence from the focal point to be recorded through the object lens because the pinhole works as a spatial filter, which can block the fluorescence from the spots that are out of focus as sown in the confocal imaging system 500 of FIG. 5 by the focal point.

Figure 6:
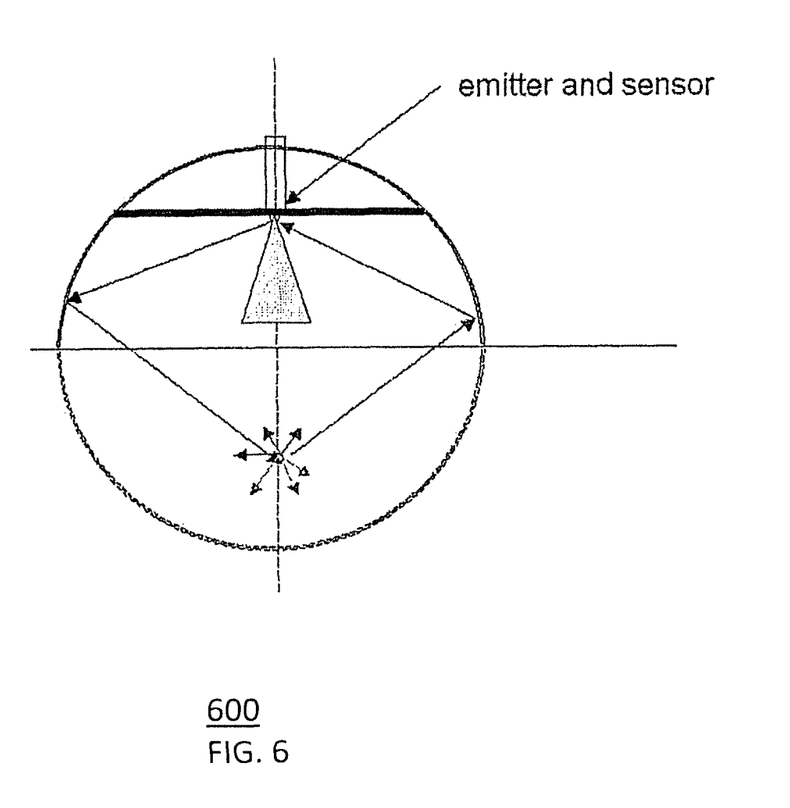
FIG. 6 is a schematic illustration of a confocal microwave imaging system.

Microwave confocal imaging can be realized through a focusing radiation system. The scattered signal at the focal point where tumor tissue is located is omni-directional. Part of the scattered waves will be acting as a secondary source and propagate back to the emitter. In this case, the conical wave launcher typically works not only as a wave radiator but also a sensor to record the backward scattering signal. Only the scattered signal from the focal point will be collected, whereas scattered signals from other objects will arrive at the first focal point at a different time. Such a concept can be found in FDTD modeling as "time gating," which can filter unwanted signals by reading the signals at different times. Thus, such radiation structure permits the radiation to be focused into the potential site, and also serves to filter other unwanted signals. This is depicted in one embodiment in the confocal microwave imaging system 600 of FIG. 6.

Figure 7A:
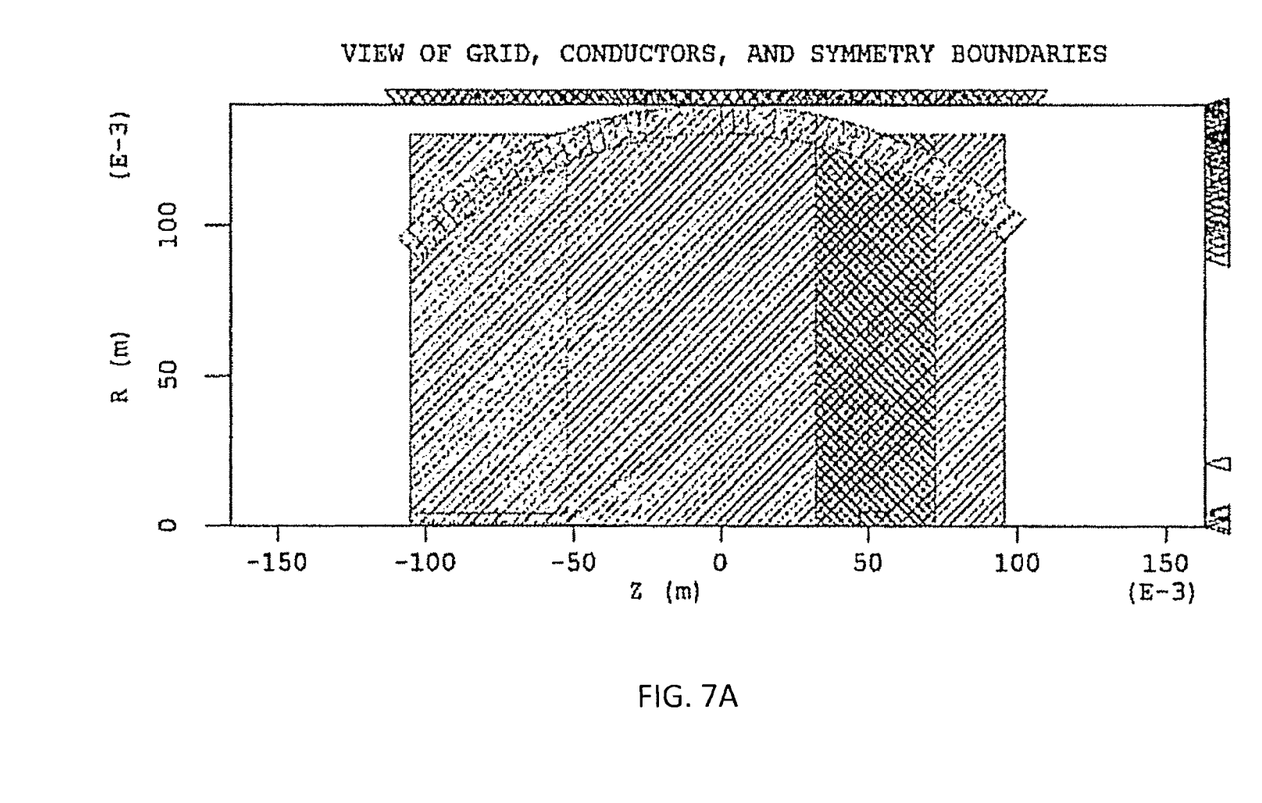
FIG. 7A depicts the configuration of the antenna, tissue and tumor.

The underlying concept can be verified by modeling, wherein the voltage is modeled at the junction of the cone apex and the coax cable feeding. As this junction is the conjugate of the second focal point, and the signal is collected. For example, using a tumor (1×1 cm) with a dielectric constant of 100 in a fat layer (10), the antenna was filled with a coupling medium which has the same dielectric constant as fat.

Figure 7B:
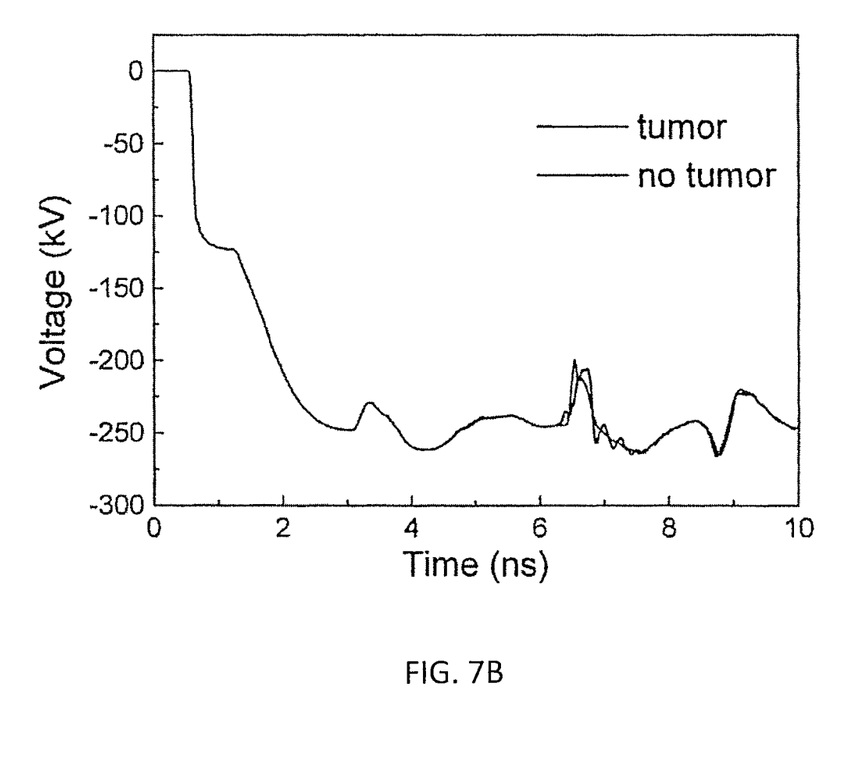
FIG. 7B depicts the focusing at the second focal point.
Figure 7C:
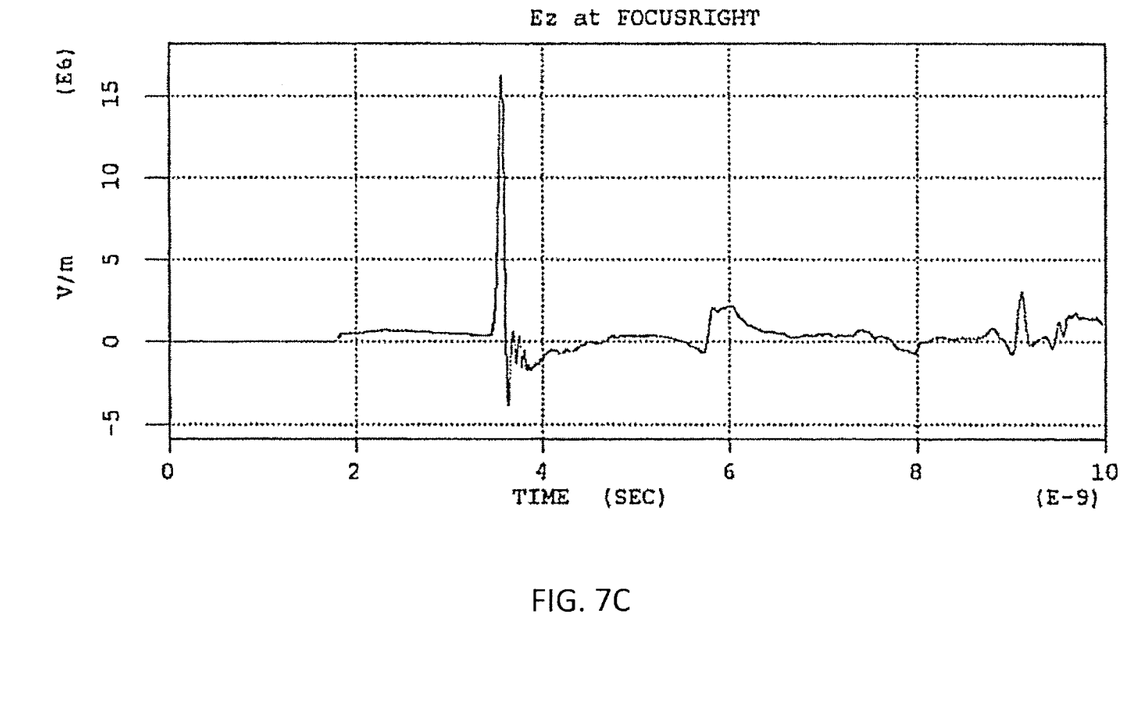
FIG. 7C depicts the voltage measure at the cone apex relative to the ground.

FIGS. 7A, 7B, and 7C illustrate the configuration of the antenna, tissue and tumor; the focusing at the second focal point; and the voltage measure at the cone apex relative to the ground. The voltage measured at the wave launcher can differentiate the signals in the tumor and non-tumor case at t=6.3 ns. This time is equal to the round trip time (2r, where r is the major radius of the prolate spheroidal reflector) from F1 to F2. This method consequently provides increased resolution.

Because of the high amplitude signal of the radiation and the consequently strong signal of the scattered signal, not only the backward scattered signal (which is the case with confocal imaging) can be recorded but also the forward scattered signal. This provides more information than a conventional approach, which only covers the reflected signal. Accordingly, the time for the image reconstruction to be reduced dramatically.

A conventional approach can be used for image reconstruction: an inverse-scattering algorithm. In the time domain, a FDTD for solving the forward scattering problem combined with optimization process can be used. By constructing a cost function, which includes all the trial values for the tissue property, a minimization process can be iterated to find all the tissue properties and form 3-D images. Because the imaging system can record the scattering in any direction, the image reconstruction process can provide fast and highly precise results.

Ultra-short pulses, (for 100 ps, 1/e amplitude, 5 GHz), can be considered as non-ionizing radiation, which is significantly safer than ionizing radiation (i.e., x-rays used in mammography.) Also, thermal effects can be substantially neglected. Non-thermal effects, for example, electric field induced electroporation, were not observed for a large number of 800 ps pulses up to a few thousand shots This instrument can be used to detect changes of dielectric properties of tissues (i.e. the permittivity, and the conductivity), which can be caused by structural and functional changes of the tissues. Tumors, for example, which have a significantly higher dielectric constant and conductivities than normal tissues, can be detected and followed over time.

The deviation of the dielectric properties of tissues from their normal states, for example, caused by external stimulations, can be monitored. For example, the function of heart, can be monitored by detecting the variations of the dielectric properties with respect to those for the healthy tissues. Injuries or illnesses which cause changes in the electrical properties of tissue can be detected and monitored.

In one embodiment, the pulses used in the imaging of the exemplary embodiments can be of high intensity. For example, using the antenna systems of the exemplary embodiments, it is possible to generate electric fields of more than about 100 kV/cm in tissue. This can allow for the exploration of tissue aberrations in deeper lying tissue, such as in liver and other organs. Due to the high intensity of the pulse, the scattered signals, which can be used to evaluate the tissue, can still have sufficient amplitude to be recorded by sensitive sensors, in spite of large losses in intensity the pulse may suffer when it passes through the tissue to reach the target and from the target to the sensor. This is in contrast to other techniques that suffer from using small signals, which allow to probe only targets close to the body surface, or targets, where the absorption is small, such as in breast tissue.

The invention, as already noted, can be realized in hardware, software, or a combination of hardware and software. The invention can be realized in a centralized fashion in one computer system, or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

The invention, as also already noted, can be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The foregoing description of preferred embodiments of the invention have been presented for the purposes of illustration. The description is not intended to limit the invention to the precise form that is disclosed. Indeed, modifications and variations will be readily apparent from the foregoing description. Accordingly, it is intended that the scope of the invention not be limited by the detailed description provided herein.

Additional aspects of the invention are described in the inventors' paper, included in U.S. Provisional Patent Application 61/015,363, filed Dec. 21, 2007, which is hereby incorporated by reference.

We claim:

1. A method of imaging and processing data, the method comprising:
   focusing radiation on a tissue site, using an antenna system comprising a an antenna feed, a conical wave launcher having its apex coupled to the antenna feed, and a reflector surrounding the conical wave launcher, where there is a predetermined probability that a tumor or other abnormality in permittivity exists;
   processing data generated in response to radiating the tissue site; and
   reconstructing an image of the tissue site based upon the processing of the data.

2. The method of claim 1, further comprising illuminating the tissue site using ultrashort electrical pulses having a duration on the order of 100 pico seconds (ps).

3. The method of claim 1, further comprising generating a spatial resolution of an image with values of 1/7 or 1/10 of a wavelength based on a non-linear algorithm.

4. The method of claim 1, further comprising implementing an image reconstruction algorithm used in an inverse scattering process.

5. The method of claim 1, further comprising illuminating the tissue site using ultrashort electrical pulses having a duration greater than 10 pico seconds (ps) and less than 1000 ps.

* * * * *